US006774113B2

(12) United States Patent
Bertho et al.

(10) Patent No.: US 6,774,113 B2
(45) Date of Patent: Aug. 10, 2004

(54) PROCESS FOR PREPARING SOLUBILIZATION ADJUVANTS FROM FUSEL OILS AND SACCHARIDES

(75) Inventors: Jean Noël Bertho, Neuflize (FR); Regis de Baynast, Versailles (FR)

(73) Assignee: Agro Industrie Recherche et Developpements (A.R.D.), Pomacle (FR)

( * ) Notice: Subject to any disclaimer, the term of this patent is extended or adjusted under 35 U.S.C. 154(b) by 48 days.

(21) Appl. No.: 10/008,791

(22) Filed: Nov. 13, 2001

(65) Prior Publication Data

US 2002/0099187 A1 Jul. 25, 2002

(30) Foreign Application Priority Data

Nov. 14, 2000 (FR) .............................. 00 14589

(51) Int. Cl.$^7$ .................. C07H 15/00; A01N 53/04; A61K 31/70; A61K 31/715
(52) U.S. Cl. .................. 514/25; 536/4.1; 536/18.5; 536/124; 536/127; 536/18.6; 514/54
(58) Field of Search .................. 514/25, 54; 536/4.1, 536/18.5, 18.6, 124, 127

(56) References Cited

U.S. PATENT DOCUMENTS

| 3,450,690 A | | 6/1969 | Gibbons et al. |
|---|---|---|---|
| 4,939,245 A | * | 7/1990 | Rasche et al. |
| 5,688,930 A | * | 11/1997 | Bertho et al. |
| 5,837,831 A | * | 11/1998 | Gruning et al. |
| 6,087,403 A | * | 7/2000 | Bertho et al. |
| 6,156,543 A | * | 12/2000 | Bertho et al. |

FOREIGN PATENT DOCUMENTS

| EP | 0 062 027 | 10/1982 |
|---|---|---|
| EP | 0 699 472 | 3/1996 |
| EP | 0 895 805 | 2/1999 |
| EP | 1 027 921 | 8/2000 |
| FR | 2 744 648 | 8/1997 |
| JP | 9315932 | 12/1997 |

* cited by examiner

Primary Examiner—James O. Wilson
Assistant Examiner—Traviss C. McIntosh, III
(74) Attorney, Agent, or Firm—Knobbe, Martens, Olson & Bear, LLP

(57) ABSTRACT

Process for preparing a solubilization adjuvant, which comprises placing fusel oils in contact with one or more reducing sugars in the presence of an acid catalyst, at a temperature of between 50° C. and 130° C. and while removing the water from the reaction medium until a solution of alkyl glycosides is obtained, and separating the glycosides from this solution.

17 Claims, No Drawings

PROCESS FOR PREPARING SOLUBILIZATION ADJUVANTS FROM FUSEL OILS AND SACCHARIDES

CROSS REFERENCE TO RELATED APPLICATIONS

This application claims priority to French patent application No. 0014589, filed Nov. 14, 2000, which is incorporated herein by reference.

FIELD OF THE INVENTION

The present invention relates to processes for manufacturing solubilization adjuvants, to their uses and to their formulations.

BACKGROUND OF THE INVENTION

Fusel oils form colourless or yellowish liquids, which have a characteristic odour. They have a density of about 0.83. Their boiling point is far from constant, since they are complex mixtures of substances with a very variable boiling point: boiling commences at about 80° C. and rises to 130–134° C.

Fusel oils are fatal co-products of alcohol fermentation. These oils, which are produced by yeast in anaerobiosis from nitrogenous materials, are recovered after rectification or on the middle plates of a column for which the alcoholic liquids have a titre of 40–50°. They are insoluble in water and are usually washed with water and separated out by settling of the phases in order to reduce the amount of ethanol they contain by about 4% to 5%. In the present invention, all the percentages are expressed on a weight basis.

Fusel oils represent on average 2% to 5% of the ethanol manufactured. As the industrial production of ethanol in France is 3 million hectoliters, not including biofuels, the potential stock is thus about 900 tonnes.

Fusel oils, occasionally referred to as "amyl oils" or "fusels", have compositions which vary depending on their origin (potato, beet, wheat, barley, etc. musts).

They are a mixture:
of 5% to 20% of water,
of 60% to 95% of alcohols mainly consisting of linear or branched alkanols containing from 2 to 5 carbon atoms,
of impurities (furfurols, ethers, fatty acids, etc.) which, in extreme cases, may be up to 15%.

The distribution of the main alkanols is as follows:

| Alkanol | Content (%) | Formula |
|---|---|---|
| Ethanol | 5 to 40 | $CH_3-CH_2-OH$ |
| 1-Propanol | 1 to 8 | $CH_3-(CH_2)_2-OH$ |
| 2-Propanol | 0 to 1 | $CH_3-CH(OH)-CH_3$ |
| 2-Methylpropanol | 5 to 15 | $CH_3-CH(CH_3)-CH_2-OH$ |
| 1-Butanol | 0 to 1 | $CH_3-(CH_2)_3-OH$ |
| 2-Methylbutanol | 10 to 30 | $CH_3-CH_2-CH(CH_3)-CH_2-OH$ |
| 3-Methylbutanol | 25 to 70 | $CH_3-CH(CH_3)-(CH_2)_2-OH$ | the combination of alkanols representing 100%.

It should be noted that fusel alcohols are natural alcohols directly produced via biotechnology in distilleries, without any intermediate chemical step.

DETAILED DESCRIPTION OF THE INVENTION

One subject of the invention is a process for preparing a solubilization adjuvant, which comprises placing fusel oils in contact with one or more reducing sugars in the presence of an acid catalyst, at a temperature of between 50° C. and 130° C. and while removing the water from the reaction medium until a solution of alkyl glycosides is obtained, and separating the glycosides from this solution.

The term "reducing sugar" means reducing saccharides chosen from aldoses such as threose, erythrose, xylose, lyxose, ribose, arabinose, glucose, galactose, mannose, idose, gulose, talose, allose or altrose; ketoses such as fructose, sorbose, erythrulose, etc.; disaccharides such as maltose, oligosaccharides and polysaccharides such as starch, dextrans, arabino-xylans, pentosans and xylans.

The term "reducing sugar" also means uronic acids such as galacturonic acid, glucuronic acid or mannuronic acid. The term "reducing sugar" furthermore means non-reducing disaccharides and oligosaccharides such as, for example, sucrose which, in the presence of an acid catalyst such as sulfuric acid, lead to reducing monosaccharides. Finally, the term "reducing sugar" means mixtures of these sugars mentioned above.

Each saccharide may be in α or β isomeric form, in L or D form, and in furanose or pyranose form.

Pentoses are preferred and most particularly L-arabinose and D-xylose which are abundantly present in the hemicelluloses of many plants.

Hexoses of the D series are also used, especially D-glucose on account of its abundance on the sugar market.

Mixtures of reducing sugars mainly consisting of D-glucose and pentoses, especially D-xylose and L-arabinose, are most particularly appreciated. Preferably, use is made of mixtures of reducing sugars derived from hemicellulose-rich and/or starch-rich agricultural co-products such as, for example, wheat straw, raw or starch-freed wheat bran, starch factory co-products as defined in patent EP 0 699 472, agricultural co-products as defined in patent EP 0 880 538 and more particularly mixtures of reducing sugars containing from 25% to 98%, preferably 60% to 100% and more particularly 90% to 100%, of pentoses and 0% to 34%, and 2% to 75%, preferably 0% to 40% and more particularly 0% to 10%, of hexoses.

The reducing sugars or mixtures of reducing sugars may be crystallized or, preferably, used in the form of syrups.

The first stage of the process according to the invention, commonly known as glycosylation, consists in placing fusel oils in contact with sugars in the presence of an acid catalyst while removing the water from the reaction medium. However, before the placing in contact, it is preferred to purify the fusel oils. This step is advantageously performed by rectification. It allows the removal of the heavy residues from the fusel oils (mainly consisting of impurities) which have boiling points of greater than 140° C. In addition to the heavy fractions, it also allows the removal of light fractions with boiling points of less than 100° C. and which consist mainly of water, ethanol, propanol and 2-methylpropanol. In general, 1 to 20 molar equivalents of alkanols are used relative to the sugars, and preferably 1.5 to 6 equivalents.

During the placing in contact, the alkanols contained in the crude or purified fusel oils are grafted onto the anomeric carbons of sugars to manufacture alkyl glycosides.

The placing in contact is performed in the presence of an acid catalyst such as sulfuric acid, a sulfonic acid such as methanesulfonic acid, hydrochloric acid or hypophosphorous acid or any other acid catalyst for carrying out a glycosidation, and mixtures thereof. This acid catalysis may also be carried out with 0.05 to 6 equivalents by weight of a sulfonic resin in its $H^+$ form or an acidic resin.

The placing in contact is carried out at a temperature of between 50° C. and 130° C. and preferably between 90° C. and 110° C, for a period of from 15 minutes to 3 hours and preferably from 1 hour to 2 hours.

In order to obtain quantitative yields, it is preferable to remove, in the course of the glycosylation, the water initially present in the starting materials or released during the reaction. This operation is advantageously performed by azeotropic distillation using a rectification column. The condensed vapours are decanted in a static decanter; the water-rich lower phase is removed and the upper phase ensures the reflux of the rectification column.

It is preferred to carry out this glycosylation reaction in the total absence of solvents, but, where appropriate, it is possible to use a solvent such as an oxide ether such as tetrahydrofuran, diethyl ether, 1,4-dioxane, isopropyl ether, methyl tert-butyl ether, ethyl tert-butyl ether or diglyme, a halogenated hydrocarbon such as methylene chloride, chloroform or 1,2-dichloroethane, a nitro solvent such as nitromethane or 2-nitropropane, a solvent of the amide of family such as N-methylformamide, N,N-dimethylformamide, N,N-dimethylacetamide or N-methyl-2-pyrrolidone, a nitrile such as acetonitrile, an alkane such as hexane, heptane or octane, or an aromatic solvent such as toluene or xylene.

The placing in contact can also be performed in the presence of microwaves.

To collect the mixture of alkyl glycosides, the process consists:

in removing the reaction solvent, if it is present, in neutralizing the acid catalyst and then in filtering off the salt obtained. The neutralization is performed, for example, using an alkali metal or alkaline-earth metal carbonate or hydrogen carbonate, especially sodium hydrogen carbonate, an alkali metal or alkaline-earth metal hydroxide, especially sodium hydroxide, or an organic base such as triethanolamine, in purifying the desired product:
  either by evaporation of the excess alkanols under a vacuum of between 0.001 and 100 mbar at a temperature of between 60° C. and 200° C., preferably using a thin-film evaporator at a pressure of from 1 to 50 mbar and a temperature of from 60° C. to 120° C.,
  or by chromatography on a column of silica gel, alumina gel, active charcoal or on ion-exchange resin,
  or, if the synthesized products allow it, by crystallization from a suitable solvent or mixture of suitable solvents chosen from oxide ethers such as tetrahydrofuran, diethyl ether, 1,4-dioxane, isopropyl ether, methyl tert-butyl ether, ethyl tert-butyl ether or diglyme, a halogenated hydrocarbon such as methylene chloride, chloroform or 1,2-dichloroethane, a nitro solvent such as nitromethane or 2-nitropropane, a solvent from the amide family such as N-methylformamide, N,N-dimethylformamide, N,N-dimethylacetamide or N-methyl-2-pyrrolidone, a nitrile such as acetonitrile, an alkane such as hexane, heptane or octane, or an aromatic solvent such as toluene or xylene,
  or by selective extractions with water-immiscible solvents, The isolated product then has a percentage of alkanols derived from the residual fusel oil of between 0% and 5% and preferably between 0% and 1%.

optionally, in dissolving the alkyl glycoside in water to obtain a solubilization adjuvant preferentially having a solids content of from 40% to 80%, if need be, in decolourizing this solubilization adjuvant by adding, at a temperature of between 15% and 100° C., 0.05% to 10% and preferably from 0.5% to 3% of hydrogen peroxide, of alkali metal or alkaline-earth metal peroxodisulfates, of perborates, persulfates, perphosphates or percarbonates, of ozone or of periodinates. 30% or 50% hydrogen peroxide is preferred. The decolourizer of the present invention should naturally be compatible with all of the ingredients of the final formulation and with the uses of the finished products.

A subject of the present invention is also adjuvants comprising, on a weight basis, with the exception of the impurities:

from 0% to 20% of a mixture of glycosides of formula (I):

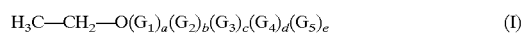

from 0% to 5% of a mixture of glycosides of formula (II):

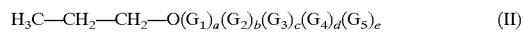

from 0% to 15% of a mixture of glycosides of formula (III):

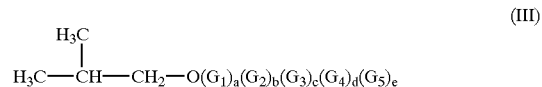

from 20% to 80% of a mixture of glycosides of formula (IV):

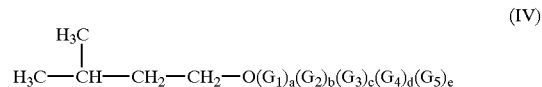

from 10% to 40% of a mixture of glycosides of formula (V):

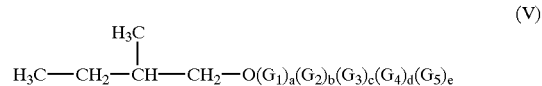

in which $G_1$, $G_2$, $G_3$, $G_4$ and $G_5$ are, independently of each other, residues of a saccharide preferentially chosen from hexoses and pentoses, these saccharides preferentially being chosen from arabinose and xylose; a, b, c, d and e being equal to 0 or 1, the sum of a, b, c, d and e being at least equal to 1. The combination of compounds I, II, III, IV and V, excluding the impurities and any alkyl glycosides other than the compounds I, II, III, IV and V, represents 100%.

On account of their efficacy and their ease of preparation, the preferred adjuvants are those which comprise at least, on a weight basis:

from 0% to 20% of a mixture of polyglycosides of formula (III), from 45% to 80% of a mixture of polyglycosides of formula (IV), from 10% to 40% of a mixture of polyglycosides of formula (V), and more particularly those which comprise, on a weight basis:

from 60% to 75% of a mixture of polyglycosides of formula (IV),
from 25% to 40% of a mixture of polyglycosides of formula (V).

In practice, there are three main routes for obtaining the adjuvants according to the invention from reducing sugars and fusel oil.

The first route consists in separately placing fusel oils in contact with a reducing sugar, in the presence of an acid catalyst, at a temperature of between 50° C. and 130° C. and while removing the water from the reaction medium, until a solution of alkyl glycosides is obtained, and in separating out the glycosides from this solution. Next, the alkyl glycosides manufactured from various reducing sugars are optionally mixed together in order to obtain the adjuvants according to the invention.

The second route consists in mixing together various reducing sugars and placing these mixtures of reducing sugars in contact with fusel oils, in the presence of an acid catalyst, at a temperature of between 50° C. and 130° C. and while removing the water from the reaction medium, until a solution of alkyl glycosides is obtained, and in separating out the glycosides from this solution in order to obtain the adjuvants according to the invention.

Finally, the third route consists in using syrups of mixtures of reducing sugars derived from starch-rich and hemicellulose-rich plant starting materials containing from 25% to 98%, preferably 60% to 100% and more particularly 90% to 100%, of pentoses and 0% to 34%, and 2% to 75%, preferably 0% to 40% and more particularly 0% to 10%, of hexoses, and in placing these syrups of reducing sugars in contact with fusel oils, in the presence of an acid catalyst, at a temperature of between 50° C. and 130° C. and while removing the water from the reaction medium until a solution of alkyl glycosides is obtained, and in separating out the glycosides from this solution in order to obtain the adjuvants according to the invention.

A subject of the present invention is also a composition comprising, on a weight basis:

10% to 60% of adjuvant or mixture of adjuvants according to the invention,
40% to 90% of nonionic, anionic, amphoteric or cationic surfactants, or mixtures thereof.

The anionic surfactants may be:
alkyl ester sulfonates of formula R—CH($SO_3M$)—COOR', in which R represents a $C_8$–$C_{20}$ and preferably $C_{10}$–$C_{16}$ alkyl radical, R' represents a $C_1$–$C_6$ and preferably $C_1$–$C_3$ alkyl radical and M represents an alkali metal (sodium, potassium or lithium) cation, a substituted or unsubstituted ammonium (methyl-, dimethyl-, trimethyl- or tetramethylammonium, dimethylpiperidinium, etc.) or an alkanolamine derivative (monoethanolamine, diethanolamine, triethanolamine, etc.);
alkyl sulfates of formula ROSO$_3$M, in which R represents a $C_{10}$–$C_{24}$, preferably $C_{12}$–$C_{20}$ and most particularly $C_{12}$–$C_{18}$ alkyl or hydroxyalkyl radical, M representing a hydrogen atom or a cation of the same definition as above, and also the ethoxylated (EO) and/or propoxylated (PO) derivatives thereof, containing on average from 0.5 to 6 and preferably from 0.5 to 3 EO and/or PO units;
alkylamide sulfates of formula RCONHR'OSO$_3$M, in which R represents a $C_2$–$C_{22}$ and preferably $C_6$–$C_{20}$ alkyl radical, R' represents a $C_2$–$C_3$ alkyl radical, M representing a hydrogen atom or a cation of the same definition as above, and also the ethoxylated (EO) and/or propoxylated (PO) derivatives thereof, containing on average from 0.5 to 60 EO and/or PO units;
alkyl-D-galactosiduronates of formula VI:

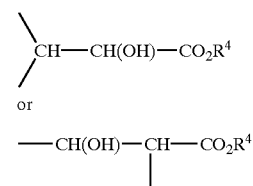

VI $R_3$ being a linear or branched alkyl radical of 6 to 22 carbon atoms and preferably of 8 to 16 carbon atoms, a hydrocarbon-based radical containing from 1 to 4 ethylenic unsaturations and from 6 to 22 carbon atoms or one of these radicals substituted with 1 to 3 substituents on different carbon atoms, chosen from hydroxyl, halogen and trifluoromethyl,
R being

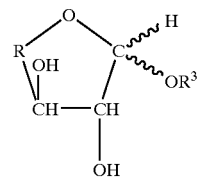

in which the carbon bearing the hydroxyl group is not linked to the endocyclic oxygen atom, $R_4$ being hydrogen, an alkali metal or alkaline-earth metal atom or a quaternary ammonium group;
saturated or unsaturated $C_8$–$C_{24}$ and preferably $C_{14}$–$C_{20}$ fatty acid salts, $C_9$–$C_{20}$ alkylbenzenesulfonates, primary or secondary $C_8$–$C_{22}$ alkyl sulfonates, alkylglyceryl sulfonates, the sulfonated polycarboxylic acids described in GB-A-1 082 179, paraffin sulfonates, N-acyl-N-alkyltaurates, alkyl phosphates, alkyl isethionates, alkyl succinamates, alkyl sulfosuccinates, sulfosuccinate monoesters or diesters, N-acyl sarcosinates, alkyl glycoside sulfates, polyethoxycarboxylates, the cation being an alkali metal (sodium, potassium or lithium), a substituted or unsubstituted ammonium residue (methyl-, dimethyl-, trimethyl- or tetramethylammonium, dimethylpiperidinium, etc.) or an alkanolamine derivative (monoethanolamine, diethanolamine or triethanolamine).

The nonionic surfactants may be:
polyoxyalkylenated (polyoxyethylenated, polyoxypropylenated or polyoxybutylenated) alkylphenols in which the alkyl substituent is $C_6$–$C_{12}$ and containing from 5 to 25 oxyalkylene units; examples which may be mentioned include the TRITON™-X (polyethylene glycol p-isooctylphenyl ether) products Triton X-45, X-114, X-100 or X-102 sold by Rohm & Haas Co.;
glucosamides and glucamides;
glycerolamides derived from N-alkylamines (U.S. Pat. No. 5,223,179 and FR-A-1 585 966); polyoxyalkylenated $C_8$–$C_{22}$ aliphatic alcohols containing from 1 to 25 oxyalkylene (oxyethylene or oxypropylene) units;

examples which may be mentioned include the TER-GITOL™ (nonylphenol polyethylene glycol ether) products Tergitol 15-S-9 and Tergitol 24-L-6 NMW sold by Union Carbide Corp., Neodol 45-9, Neodol 23-65, Neodol 45-7 and Neodol 45-4 sold by Shell Chemical Co., and Kyro EOB sold by The Procter & Gamble Co.;

products resulting from the condensation of ethylene oxide with a hydrophobic compound resulting from the condensation of propylene oxide with propylene glycol, such as PLURONIC™ (block copolymers of ethylene oxide and propylene oxide) products sold by BASF;

products resulting from the condensation of ethylene oxide, or the compound resulting from the condensation of propylene oxide, with ethylenediamine, such as the TETRONIC™ (block copolymers derived from addition of ethylene oxide and propylene oxide to ethylene diamine) products sold by BASF;

amine oxides such as $C_{10}$–$C_{18}$ alkyl dimethylamine oxides and $C_8$–$C_{22}$ alkoxy ethyl dihydroxy ethylamine oxides;

the alkyl polyglycosides of formula VII below:

$$R^5O(A_1)_f(A_2)_g(A_3)_h(A_4)_i(A_5)_j \qquad (VII)$$

in which $A_1$, $A_2$, $A_3$, $A_4$ and $A_5$ are, independently of each other, residues of a saccharide chosen from hexoses and more particularly D-glucose; pentoses, the latter preferentially being chosen from arabinose and xylose; f, g, h, i and j being equal to 0 or 1, the sum of f, g, h, i and j being at least equal to 1; $R^5$ being a linear or branched alkyl radical of 6 to 22 carbon atoms, a hydrocarbon-based radical containing from 1 to 4 ethylenic unsaturations and from 6 to 22 carbon atoms or one of these radicals substituted with 1 to 3 substituents on different carbon atoms, chosen from hydroxyl, halogen and trifluoromethyl;

$C_8$–$C_{20}$ fatty acid amides;

ethoxylated fatty acids;

ethoxylated fatty amides;

ethoxylated amities.

The lipophilic active substances to be dissolved may be:

essential oils such as, for example, cluster pine oil or Scotch pine oil, oils of citrus plants such as lemon, grapefruit, orange or mandarin, cereal oils such as wheat gluten oil, wheat germ oil, aniseed oil, bitter almond oil, birch oil, camomile oil, bergamot oil, cinnamon oil or lemongrass oil, oils of aromatic plants such as white thyme, red thyme, rosemary, mint, eucalyptus, basil, tarragon, laurel, oregano or vervain, juniper oil, clove oil, iavender oil, geranium oil, cedar oil, coriander oil, common juniper oil, everlasting oil and marjoram oil;

synthetic aromatic products such as, for example, aromatic esters, for instance benzyl, linalyl, terpenyl, vetiveryl, amyl, bornyl, cedryl, geranyl, phenylethyl, para-cresyl or styrallyl acetate, amyl butyrates, eugenol, geraniol, anisyl alcohol, cinnamyl alcohol, styrallyl alcohol, aldehydes such as octyl, nonyl, decyl, undecylenyl, lauryl, myristyl, cetyl and stearyl aldehyde, benzaldehyde and anisaldehyde, synthetic camphor and limonene;

natural or synthetic fragrances;

lipophilic cosmetic adjuvants;

glycolipids such as, for example, sophorose lipids;

preserving agents such as the methyl, ethyl, propyl and butyl esters of p-hydroxybenzoic acid, sodium benzoate, GERMABEN™ (diazolidinyl urea) or any chemical agent for preventing bacterial or mold proliferation which is traditionally used in cosmetic compositions are generally introduced into these compositions to a proportion of 0.01% to 3% by weight;

UV-A active and/or UV-B active organic sunscreens for protecting the skin or the hair against attack from sunlight and UV rays, for instance the compounds permitted in European Directive No. 76/768/EEC, its appendices and the subsequent modifications of this directive;

insect repellents;

vitamins;

The cationic surfactants may be, for example, alkyldimethylammonium halides.

The amphoteric and zwitterionic surfactants may be:

alkyldimethylbetaines, alkylamidopropyldimethylbetaines, alkyltrimethylsulfobetaines, the products of condensation of fatty acids and of protein hydrolysates.

The compositions according to the invention make it possible to increase the solubility of lipophilic molecules in water. The lipophilic molecules may be:

essential oils such as, for example, cluster pine oil or Scotch pine oil, oils of citrus plants such as lemon, grapefruit, orange or mandarin, cereal oils such as wheat gluten oil, wheat germ oil, aniseed oil, bitter almond oil, birch oil, camomile oil, bergamot oil, cinnamon oil or lemongrass oil, oils of aromatic plants such as white thyme, red thyme, rosemary, mint, eucalyptus, basil, tarragon, laurel, oregano or vervain, juniper oil, clove oil, lavender oil, geranium oil, cedar oil, coriander oil, common juniper oil, everlasting oil, marjoram oil, etc.;

synthetic aromatic products such as, for example, aromatic esters, for instance benzyl, linalyl, terpenyl, vetiveryl, amyl, bornyl, cedryl, geranyl, phenylethyl, para-cresyl or styrallyl acetate, amyl butyrates, eugenol, geraniol, anisyl alcohol, cinnamyl alcohol, styrallyl alcohol, aldehydes such as octyl, nonyl, decyl, undecylenyl, lauryl, myristyl, cetyl and stearyl aldehyde, benzaldehyde and anisaldehyde, synthetic camphor and limonene;

natural or synthetic fragrances;

lipophilic cosmetic adjuvants;

glycolipids such as, for example, sophorose lipids;

preserving agents such as the methyl, ethyl, propyl and butyl esters of p-hydroxybenzoic acid, sodium benzoate, Germaben® or any chemical agent for preventing bacterial or mould proliferation which is traditionally used in cosmetic compositions are generally introduced into these compositions to a proportion of 0.01% to 3% by weight;

UV-A active and/or UV-B active organic sunscreens for protecting the skin or the hair against attack from sunlight and UV rays, for instance the compounds permitted in European Directive No. 76/768/EEC, its appendices and the subsequent modifications of this directive;

antioxidants;

insect repellents;

vitamins;

colorants;

plant-protection active materials, for instance herbicides, fungicides and insecticides, such as those described in The Pesticide Manual ($9^{th}$ edition, C. R. Workling and R. J. Hance, editors, published by The British Crop Protection Council). Formulation adjuvants furthermore make it possible to facilitate the penetration of pesticides into the plant, which increases their efficacy and thus enables their working dose to be reduced;

rapeseed methyl ester;

proteins;

lipophilic pharmaceutical ingredients, etc.

The increase in the solubility of these lipophilic molecules in water is due to the incorporation of lipophilic products into the micelles of the surfactants or their incorporation into a less ordered molecular organization, forming a hydrotropic medium.

The compositions that are preferred according to the invention are those comprising:

10% to 60% of adjuvant according to the invention,

40% to 90% of nonionic surfactants such as those mentioned above.

The ones most particularly preferred, especially on account of their efficacy, their good biodegradability, their low irritant power and their good ecotoxicity, are the compositions according to the invention comprising:

10% to 60% of adjuvant according to the invention,

40% to 90% of alkyl polyglycosides of formula VII described in patent EP 0 699 472:

$$R^5\text{---}O(A_1)_f(A_2)_g(A_3)_h(A_4)_i(A_5)_j \quad \text{(VII)}$$

in which $A_1$, $A_2$, $A_3$, $A_4$ and $A_5$ are, independently of each other, residues of a saccharide chosen from hexoses and more particularly D-glucose; pentoses, the latter being chosen preferentially from arabinose and xylose; f, g, h, i and j being equal to 0 or 1; the sum of f, g, h, i and j being at least equal to 1; $R^5$ being a linear or branched alkyl radical of 6 to 22 carbon atoms, a hydrocarbon-based radical containing from 1 to 4 ethylenic unsaturations and from 6 to 22 carbon atoms, or one of these radicals substituted with 1 to 3 substituents on different carbon atoms, chosen from hydroxyl, halogen and trifluoromethyl. Preference is given most particularly to alkyl polyglycosides containing from 8 to 16 carbon atoms on the alkyl radical $R^5$; and especially mixtures of octyl and decyl polyglycosides, mixtures of decyl and dodecyl polyglycosides, mixtures of dodecyl and tetradecyl polyglycosides, mixtures of octyl, decyl, dodecyl and tetradecyl polyglycosides and mixtures of dodecyl, tetradecyl and hexadecyl polyglycosides.

A subject of the present invention is also a clear composition comprising, on a weight basis:

0.5% to 5% of adjuvant according to the invention,

2% to 7% of alkyl polyglycosides of formula VII containing from 8 to 14 carbon atoms on the alkyl chain $R^5$;

1% to 10% of linear or branched alkanols containing from 2 to 5 carbon atoms, or mixtures thereof, 0.1% to 3% of lipophilic active substances to be dissolved.

As examples of linear or branched alkanols containing from 2 to 5 carbon atoms, mention may be made of ethanol, 2-propanol, n-butanol, 2-methylpropanol, 2-methylbutanol, 3-methylbutanol, n-pentanol and the alkanols contained in fusel oils.

colorants;

plant-protection active materials, for instance herbicides, fungicides and insecticides, such as those described in the Pesticide Manual ($9^{th}$ edition, C. R. Workling and R. J. Hance, editors, published by The British Crop Protection Council);

rapeseed methyl ester;

proteins;

lipophilic pharmaceutical ingredients, etc.

The compositions that are most particularly preferred according to the invention are those comprising, on a weight basis:

0.5% to 5% of adjuvant according to the invention,

1% to 10% of alkyl polyglycosides containing from 8 to 14 carbon atoms on the alkyl chain, 1% to 10% of linear or branched alkanols containing from 2 to 5 carbon atoms, or mixtures thereof, 0.1% to 2% of essential oil, 0 to 0.5% of preserving agent, for instance the methyl, ethyl, and butyl esters of p-hydroxybenzoic acid, sodium benzoate, GERMABEN™ (diazolidinyl urea)® or any chemical agent for preventing bacterial or mold proliferation which is traditionally used in cosmetic and detergent compositions.

These compositions are particularly effective for washing smooth surfaces and constitute high-quality, biodegradable, environmentally friendly multi-purpose detergents.

In general, the adjuvants according to the invention may be present in formulations such as detergents in powder or liquid form, foaming or non-foaming lotions, emulsions of liquid or semi-liquid consistency such as milks obtained by dispersing a fatty phase in an aqueous phase or vice versa, suspensions or emulsions of soft consistency such as creams or ointments, gels or alternatively solid preparations such as cleansing sticks and bars, impregnated pads or moisturizing masks.

The adjuvants according to the invention may especially be present in:

household and industrial detergents, for instance multi-purpose cleaning agents, washing-up products or floor, window, bathroom or textile cleaning products;

cosmetic formulations, for instance lotions, cleansing milks, make-up-removing compositions, care creams, creams or lotions for protecting against sunlight and ultraviolet radiation, styling mousses or gels or any formulation used for hairstyling or to make the hair easier to comb, hair or body shampoos, facial or body cleansing gels, liquid soap, bubble bath compositions, formulations used for cleaning the teeth or the oral cavity, for instance mouthwashes or toothpastes, and cleansing soaps or bars;

plant-protection formulations.

The examples which follow are intended to illustrate the present invention.

EXAMPLE 1

Synthesis of Solubilization Adjuvant From D-xylose and Fusel Oils 1277 g of fusel oil having the composition below:

| Constituent | % |
|---|---|
| Water | 10.0 |
| Ethanol | 6.0 |
| 2-Propanol | 0.2 |
| 1-Propanol | 2.1 |
| 2-Methylpropanol | 9.3 |
| 1-Butanol | 0.3 |
| 3-Methylbutanol | 45.0 |
| 2-Methylbutanol | 20.3 |
| Impurities | 6.8 | are boiled in a boiling vessel on which is mounted a rectification column. A fraction A with boiling points of less than 100° C. (204 g) is collected in a first stage, followed by collection, in a second stage, of a fraction B with boiling points of between 100° C. and 140° C. (994 g) having the composition below:

| Constituent | % |
|---|---|
| Water | 6 |
| Ethanol | 3.2 |
| 2-Propanol | 0.2 |
| 1-Propanol | 2 |
| 2-Methylpropanol | 10.1 |
| 1-Butanol | 0.3 |
| 3-Methylbutanol | 55.3 |
| 2-Methylbutanol | 21 |
| Impurities | 1.9 |

170 g of D-xylose are placed in 630 g of fraction B containing 3.4 g of sulfuric acid. The reaction medium is maintained under reduced pressure for 3 hours at 100° C. The water is removed by azeotropic distillation during the reaction. The acidity of the medium is neutralized with aqueous 30.5% sodium hydroxide solution to pH 7 to 8. The excess fusel alcohols are evaporated off under reduced pressure at 80° C. The residue (244 g) is dissolved in 100 g of osmosed water. The alkyl xylosides obtained are decolourized in the presence of 5 g of 50% aqueous hydrogen peroxide solution at neutral pH.

EXAMPLE 2

Synthesis of Adjuvant From L-arabinose and Fusel Oils 1441 g of fusel oil having the composition below:

| Constituent | % |
|---|---|
| Water | 16.1 |
| Ethanol | 22.6 |
| 2-Propanol | 0.2 |
| 1-Propanol | 2.6 |
| 2-Methylpropanol | 6.7 |
| 1-Butanol | 0.3 |
| 3-Methylbutanol | 23.0 |
| 2-Methylbutanol | 10.5 |
| Impurities | 18.0 | are boiled in a boiling vessel on which is mounted a rectification column. A fraction A with boiling points of less than 100° C. (594 g) is collected in a first stage, followed by collection, in a second stage, of a fraction B with boiling points of between 100° C. and 140° C., which separates out by settling. The upper phase C (582 g) has the composition below:

| Constituent | % |
|---|---|
| Water | 9.9 |
| Ethanol | 10.8 |
| 2-Propanol | 0 |
| 1-Propanol | 2.8 |
| 2-Methylpropanol | 9.2 |
| 1-Butanol | 0.6 |
| 3-Methylbutanol | 40.8 |
| 2-Methylbutanol | 18.4 |
| Impurities | 7.5 |

200 g of L-arabinose are placed in 774 g of fraction C containing 4 g of sulfuric acid. The reaction medium is maintained under reduced pressure for 3 hours at 100° C. The water is removed by azeotropic distillation during the reaction. The acidity of the medium is neutralized with aqueous 30.5% sodium hydroxide solution to pH 7 to 8. The excess fusel alcohols are evaporated off under reduced pressure at 80° C. The residue (282 g) is dissolved in 120 g of osmosed water. The alkyl arabinosides obtained are decolourized in the presence of 5 g of 50% aqueous hydrogen peroxide solution at neutral pH.

EXAMPLE 3

Synthesis of Adjuvant From D-glucose and Fusel Oils 1277 g of fusel oil having the composition below:

| Constituent | % |
|---|---|
| Water | 10.0 |
| Ethanol | 6.0 |
| 2-Propanol | 0.2 |
| 1-Propanol | 2.1 |
| 2-Methylpropanol | 9.3 |
| 1-Butanol | 0.3 |
| 3-Methylbutanol | 45.0 |
| 2-Methylbutanol | 20.3 |
| Impurities | 6.8 | are boiled in a boiling vessel on which is mounted a rectification column. A fraction A with boiling points of less than 100° C. (204 g) is collected in a first stage, followed by collection, in a second stage, of a fraction B with boiling points of between 100° C. and 140° C. (994 g) having the composition below:

| Constituent | % |
|---|---|
| Water | 6 |
| Ethanol | 3.2 |
| 2-Propanol | 0.2 |
| 1-Propanol | 2 |
| 2-Methylpropanol | 10.1 |
| 1-Butanol | 0.3 |
| 3-Methylbutanol | 55.3 |
| 2-Methylbutanol | 21 |
| Impurities | 1.9 |

200 g of D-glucose monohydrate are placed in 562 g of fraction B containing 3.6 g of sulfuric acid. The reaction medium is maintained under reduced pressure for 3 hours at 100° C. The water is removed by azeotropic distillation during the reaction. After filtration, the acidity of the medium is neutralized with aqueous 30.5% sodium hydroxide solution to pH 7 to 8. The excess fusel alcohols are evaporated off under reduced pressure at 80° C. The residue (244 g) is dissolved in 100 g of osmosed water. The alkyl glucosides obtained are decolourized in the presence of 5 g of 50% aqueous hydrogen peroxide solution at neutral pH.

EXAMPLE 4

Synthesis of Adjuvant from Mixtures of D-xylose, L-arabinose and D-glucose and Fusel Oils 1277 g of fusel oil having the composition below:

| Constituent | % |
|---|---|
| Water | 10.0 |
| Ethanol | 6.0 |
| 2-Propanol | 0.2 |
| 1-Propanol | 2.1 |
| 2-Methylpropanol | 9.3 |
| 1-Butanol | 0.3 |
| 3-Methylbutanol | 45.0 |
| 2-Methylbutanol | 20.3 |
| Impurities | 6.8 | are boiled in a boiling vessel on which is mounted a rectification column. A fraction A with boiling points of less than 100° C. (204 g) is collected in a first stage, followed by collection, in a second stage, of a fraction B with boiling points of between 100° C. and 140° C. (994 g) having the composition below:

| Constituent | % |
|---|---|
| Water | 6 |
| Ethanol | 3.2 |
| 2-Propanol | 0.2 |
| 1-Propanol | 2 |
| 2-Methylpropanol | 10.1 |
| 1-Butanol | 0.3 |
| 3-Methylbutanol | 55.3 |
| 2-Methylbutanol | 21 |
| Impurities | 1.9 |

100 g of D-xylose, 100 g of L-arabinose and 100 g of anhydrous D-glucose are placed in 1050 g of fraction B containing 6 g of sulfuric acid. The reaction medium is maintained under reduced pressure for 3 hours at 100° C. The water is removed by azeotropic distillation during the reaction. The acidity of the medium is neutralized with aqueous 30.5% sodium hydroxide solution to pH 7 to 8. The excess fusel alcohols are evaporated off under reduced pressure at 80° C. The residue (420 g) is dissolved in 180 g of osmosed water. The alkyl glycosides obtained are decolourized in the presence of 12 g of 50% aqueous hydrogen peroxide solution at neutral pH.

EXAMPLE 5

Synthesis of Adjuvant From Sugar Syrups Derived From Wheat Straw and Fusel Oils 1500 g of fusel oil having the composition below:

| Constituent | % |
|---|---|
| Water | 10.0 |
| Ethanol | 6.0 |
| 2-Propanol | 0.2 |
| 1-Propanol | 2.1 |
| 2-Methylpropanol | 9.3 |
| 1-Butanol | 0.3 |
| 3-Methylbutanol | 45.0 |
| 2-Methylbutanol | 20.3 |
| Impurities | 6.8 | are boiled in a boiling vessel on which is mounted a rectification column. A fraction A with boiling points of less than 100° C. (242 g) is collected in a first stage, followed by collection, in a second stage, of a fraction B with boiling points of between 100° C. and 140° C. (1160 g) having the composition below:

| Constituent | % |
|---|---|
| Water | 6 |
| Ethanol | 3.2 |
| 2-Propanol | 0.2 |
| 1-Propanol | 2 |
| 2-Methylpropanol | 10.1 |
| 1-Butanol | 0.3 |
| 3-Methylbutanol | 55.3 |
| 2-Methylbutanol | 21 |
| Impurities | 1.9 |

150 g of sugar syrup derived from wheat straw and containing 37.5 g of water, 79 g of D-xylose, 13.6 g of L-arabinose, 8 g of D-glucose and 4.5 g of D-galactose and D-mannose are added dropwise over 1 hour 30 minutes to 400 g of fraction B containing 2.25 g of sulfuric acid, at a temperature of about 100° C. to 107° C. The water is removed during the reaction by azeotropic distillation. After the addition of the sugar syrup, the pressure of the reaction medium is gradually lowered to between 300 and 900 mbar at the same temperature so as to remove the traces of water.

The acidity of the medium is then neutralized with aqueous 30.5% sodium hydroxide solution to pH 7 to 8. The excess fusel alcohols are evaporated off under reduced pressure at 80° C. The residue (155 g) is dissolved in 65 g of osmosed water. The alkyl glycosides obtained are decolourized in the presence of 5 g of 50% aqueous hydrogen peroxide solution at neutral pH.

EXAMPLE 6

Synthesis of Adjuvant From Sugar Syrups Extracted From Starch-freed Wheat Bran and Fusel Oils 1277 g of fusel oil having the composition below:

| Constituent | % |
|---|---|
| Water | 10.0 |
| Ethanol | 6.0 |
| 2-Propanol | 0.2 |
| 1-Propanol | 2.1 |
| 2-Methylpropanol | 9.3 |
| 1-Butanol | 0.3 |
| 3-Methylbutanol | 45.0 |
| 2-Methylbutanol | 20.3 |
| Impurities | 6.8 | are boiled in a boiling vessel on which is mounted a rectification column. A fraction A with boiling points of less than 100° C. (204 g) is collected in a first stage, followed by collection, in a second stage, of a fraction B with boiling points of between 100° C. and 140° C. (994 g) having the composition below:

| Constituent | % |
|---|---|
| Water | 6 |
| Ethanol | 3.2 |
| 2-Propanol | 0.2 |
| 1-Propanol | 2 |
| 2-Methylpropanol | 10.1 |
| 1-Butanol | 0.3 |
| 3-Methylbutanol | 55.3 |
| 2-Methylbutanol | 21 |
| Impurities | 1.9 |

200 g of sugar syrup derived from starch-freed wheat bran and containing 50 g of water, 72 g of D-xylose, 42 g of L-arabinose, 10.4 g of D-glucose and 3.7 g of D-galactose and D-mannose are added dropwise over 1 hour 30 minutes to 525 g of fraction B containing 3 g of sulfuric acid, at a temperature of about 100° C. to 105° C. The water is removed during the reaction by azeotropic distillation. After the addition of the sugar syrup, the pressure of the reaction medium is gradually lowered to between 300 and 900 mbar at the same temperature so as to remove the traces of water. The acidity of the medium is then neutralized with aqueous 30.5% sodium hydroxide solution to pH 7 to 8. The excess fusel alcohols are evaporated off under reduced pressure at 80° C. The residue (207 g) is dissolved in 90 g of osmosed water. The alkyl glycosides obtained are decolourized in the presence of 6 g of 50% aqueous hydrogen peroxide solution at neutral pH.

EXAMPLE 7

Synthesis of Adjuvant from Sugar Syrups Extracted From Raw Wheat Bran and Fusel Oils 1277 g of fusel oil having the composition below:

| Constituent | % |
|---|---|
| Water | 10.0 |
| Ethanol | 6.0 |
| 2-Propanol | 0.2 |
| 1-Propanol | 2.1 |
| 2-Methylpropanol | 9.3 |
| 1-Butanol | 0.3 |
| 3-Methylbutanol | 45.0 |
| 2-Methylbutanol | 20.3 |
| Impurities | 6.8 | are boiled in a boiling vessel on which is mounted a rectification column. A fraction A with boiling points of less than 100° C. (204 g) is collected in a first stage, followed by collection, in a second stage, of a fraction B with boiling points of between 100° C. and 140° C. (994 g) having the composition below:

| Constituent | % |
|---|---|
| Water | 6 |
| Ethanol | 3.2 |
| 2-Propanol | 0.2 |
| 1-Propanol | 2 |
| 2-Methylpropanol | 10.1 |
| 1-Butanol | 0.3 |
| 3-Methylbutanol | 55.3 |
| 2-Methylbutanol | 21 |
| Impurities | 1.9 |

200 g of sugar syrup derived from raw wheat bran and containing 50 g of water, 34.5 g of D-xylose, 20 g of L-arabinose, 71 g of D-glucose and 2 g of D-galactose and D-mannose are added dropwise over 1 hour 30 minutes to 470 g of fraction B containing 3 g of sulfuric acid, at a temperature of about 100° C. to 105° C. The water is removed during the reaction by azeotropic distillation. After the addition of the sugar syrup, the pressure of the reaction medium is gradually lowered to between 300 and 900 mbar at the same temperature so as to remove the traces of water. The acidity of the medium is then neutralized with aqueous 30.5% sodium hydroxide solution to pH 7 to 8. The excess fusel alcohols are evaporated off under reduced pressure at 80° C. The residue (202 g) is dissolved in 90 g of osmosed water. The alkyl glycosides obtained are decolourized in the presence of 8 g of 50% aqueous hydrogen peroxide solution at neutral pH.

EXAMPLE 8

Synthesis of Adjuvant From D-xylose and Fusel Oils 150 g of D-xylose are placed in 740 g of fusel oil having the composition below:

| Constituent | % |
|---|---|
| Water | 10.0 |
| Ethanol | 6.0 |
| 2-Propanol | 0.2 |
| 1-Propanol | 2.1 |
| 2-Methylpropanol | 9.3 |
| 1-Butanol | 0.3 |
| 3-Methylbutanol | 45.0 |
| 2-Methylbutanol | 20.3 |
| Impurities | 6.8 | and containing 7.5 g of sulfuric acid. The reaction medium is maintained under reduced pressure for 1 hour at 110° C. The water is removed by azeotropic distillation during the reaction. The acidity of the medium is neutralized with aqueous 30.5% sodium hydroxide solution to pH 7 to 8. The excess fusel alcohols are evaporated off under reduced pressure at 80° C. The residue (200 g) is dissolved in 100 g of osmosed water. The alkyl xylosides obtained are decolourized in the presence of 10 g of 50% aqueous hydrogen peroxide solution at neutral pH.

EXAMPLE 9

Solubilization Adjuvant 50 g of solubilization adjuvant of Example 1 are mixed, with stirring, with 25 g of solubilization adjuvant of Example 2 and 25 g of solubilization adjuvant of Example 3 so as to obtain a novel solubilization adjuvant.

EXAMPLE 10

Solubilization Adjuvant 85 g of solubilization adjuvant of Example 1 are mixed, with stirring, with 15 g of solubilization adjuvant of Example 3 so as to obtain a novel solubilization adjuvant.

EXAMPLE 11

Solubilization Adjuvant 31 g of solubilization adjuvant of Example 1 are mixed, with stirring, with 69 g of solubilization adjuvant of Example 3 so as to obtain a novel solubilization adjuvant.

EXAMPLE 12

Solubilizing Composition 30 g of solubilization adjuvant of Example 10 are mixed, with stirring, with 70 g of alkyl polyglycosides as prepared in Example 9 of patent EP 0 699 472 so as to obtain a solubilizing composition.

EXAMPLE 13

Solubilizing Composition 30 g of solubilization adjuvant of Example 11 are mixed, with stirring, with 70 g of alkyl polyglycosides as prepared in Example 9 of patent EP 0 699 472 so as to obtain a solubilizing composition.

EXAMPLE 14

Solubilizing Composition 40 g of solubilization adjuvant of Example 5 are mixed, with stirring, with 60 g of alkyl polyglycosides as prepared in Example 6 of patent EP 0 699 472 so as to obtain a solubilizing composition.

EXAMPLE 15

Solubilizing Composition 25 g of solubilization adjuvant of Example 6 are mixed, with stirring, with 75 g of alkyl polyglycosides as prepared in Example 9 of patent EP 0 699 472 so as to obtain a solubilizing composition.

EXAMPLE 16

Solubilizing Composition 30 g of solubilization adjuvant of Example 1 are mixed, with stirring, with 60 g of alkyl polyglycosides as prepared in Example 9 of patent EP 0 699 472 so as to obtain a solubilizing composition.

EXAMPLE 17

Solubilization of a Synthetic Lemon Fragrance

100 μl of water-insoluble lemon 19-11454 synthetic fragrance from Huber the Nose are suspended in 5 ml of osmosed water containing the solubilizing composition of Example 12. 8.4 g of solubilizing composition of Example 12 allow 1 g of fragrance to be dissolved. A perfectly clear solution is thus obtained after stirring for 1 minute.

EXAMPLE 18

Solubilization of a Synthetic Marine Fragrance

100 μl of water-insoluble marine fragrance 813417F are suspended in 5 ml of osmosed water containing the solubilizing composition of Example 12. 7.4 g of solubilizing composition of Example 12 allow 1 g of fragrance to be dissolved. A perfectly clear solution is thus obtained after stirring for 1 minute.

EXAMPLE 19

Solubilization of Rapeseed Methyl Ester

100 μl of water-insoluble rapeseed methyl ester (Total Radia 7961) are suspended in 5 ml of osmosed water containing the solubilizing composition of Example 13. 5.4 g of solubilizing composition of Example 13 allow 1 g of rapeseed methyl ester to be dissolved. A perfectly clear solution is thus obtained after stirring for 1 minute.

EXAMPLE 20

Solubilization of 1-decanol

100 μl of water-insoluble decanol are suspended in 5 ml of osmosed water containing the solubilizing composition of Example 13. 6.5 g of solubilizing composition of Example 13 allow 1 g of decanol to be dissolved. A perfectly clear solution is thus obtained after stirring for 1 minute.

EXAMPLE 21

Solubilization of Isopropyl Myristate

100 μl of water-insoluble isopropyl myristate are suspended in 5 ml of osmosed water containing the solubilizing composition of Example 12. 10 g of solubilizing composition of Example 12 allow 1 g of isopropyl myristate to be dissolved. A perfectly clear solution is thus obtained after stirring for 1 minute.

EXAMPLE 22

Solubilization of Essential Oil of Rosemary

100 μl of water-insoluble essential oil of rosemary are suspended in 5 ml of osmosed water containing the solubilizing composition of Example 12. 5.9 g of solubilizing composition of Example 12 allow 1 g of essential oil of rosemary to be dissolved. A perfectly clear solution is thus obtained after stirring for 1 minute.

EXAMPLE 23

Clear Composition

A clear composition is prepared by mixing together:
7.1 g of solubilizing composition of Example 12
3 g of ethanol
0.3 g of lemon 19-11454 lemon fragrance from Huber the Nose
0.4 g of preserving agent (Phenonip®)
Osmosed water qs 100 g

EXAMPLE 24

Clear Detergent Composition

A clear composition is prepared by mixing together:
8.6 g of solubilizing composition of Example 15
4 g of ethanol
0.5 g of essential oil of pine 34230 (OSF)
0.4 g of preserving agent (Phenonip®)
Osmosed water qs 100 g
This composition has excellent multi-purpose detergent properties, especially for washing smooth surfaces.

EXAMPLE 25

Clear Detergent Composition

A clear composition is prepared by mixing together:
8.1 g of solubilizing composition of Example 15
0.3 g of sodium dodecyl sulfate
3 g of ethanol
0.5 g of essential oil of pine 34230 (OSF)
0.4 g of preserving agent (Phenonip®)
Osmosed water qs 100 g
This composition has excellent multi-purpose detergent properties, especially for washing smooth surfaces.

EXAMPLE 26

Clear Detergent Composition

A clear composition is prepared by mixing together:
8.6 g of solubilizing composition of Example 15
3 g of ethanol
0.5 g of essential oil of lemon 9286 (OSF)
0.4 g of preserving agent (Phenonip®)
Osmosed water qs 100 g
This composition has excellent multi-purpose detergent properties, especially for washing smooth surfaces.

EXAMPLE 27

Clear Detergent Composition

A clear composition is prepared by mixing together:
8.1 g of solubilizing composition of Example 15
0.3 g of sodium dodecyl sulfate
3 g of ethanol
0.5 g of essential oil of lemon 9286 (OSF)
0.4 g of preserving agent (Phenonip®)
Osmosed water qs 100 g
This composition has excellent multi-purpose detergent properties, especially for washing smooth surfaces.

What is claimed is:

1. A process for preparing a solubilization adjuvant, comprising:
removing the light fractions from the fusel oils which have boiling points of less than 100° C.;
placing fusel oils in contact with one or more reducing sugars in the presence of an acid catalyst, at a temperature of between 50° C. and 130° C. while removing the water from the reaction medium;
obtaining a solution of alkyl glycosides; and
separating the glycosides from this solution.

2. The process according to claim 1, comprising, before the placing in contact with one or more reducing sugars, removing the heavy fractions from the fusel oils which have boiling points of greater than 140° C.

3. The process according to claim 2 comprising removing the heavy fractions from the fusel oils which have boiling points of greater than 140° C., by dilation.

4. The process according to claim 1 comprising removing the light fractions from the fusel oils which have boiling points of less than 100° C., by distillation.

5. The process according to claim 1, comprising using, as reducing sugars, pentoses selected from the group consisting of L-arabinose and D-xylose.

6. The process according to claim 1, comprising using glucose as reducing sugar.

7. The process according to claim 1, comprising using, as reducing sugars, sugar mixtures comprising, on a weight basis, from 25% to 100% of pentoses selected from the group consisting of L-arabinose and D-xylose, and 0% to 75% of hexoses selected from the group consisting of D-glucose, D-galactose and D-mannose.

8. An adjuvant, comprising, on a weight basis:
from 0% to 20% of a mixture of polyglycosides of formula (I):

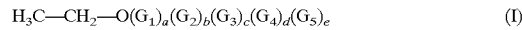

from 0% to 5% of a mixture of polyglycosides of formula (II):

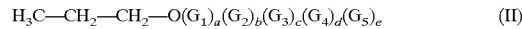

from 0% to 15% of a mixture of polyglycosides of formula (III):

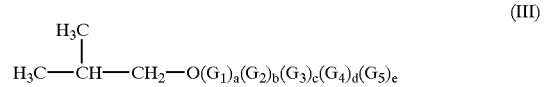

from 20% to 80% of a mixture of polyglycosides of formula (IV):

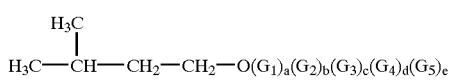

(IV)

from 10% to 40% of a mixture of polyglycosides of formula (V):

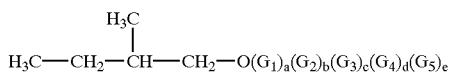

(V)

in which $G_1$, $G_2$, $G_3$, $G_4$, and $G_5$ are, independently of each other, residues of a saccharide selected from the group consisting of hexoses and pentoses; a, b, c, d, and e being equal to 0 or 1, the sum of a, b, c, d, and e being at least equal to 1 and wherein the combination of compounds I, II, III, IV, sad V, excluding any alkyl glycosides other than the compounds I, II, III, IV and V, represents 100%.

9. An adjuvant comprising at least, on a weight basis:

from 0% to 20 % of a mixture of polyglycosides of formula (I):

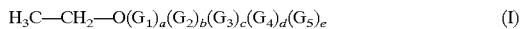

(I)

from 0% to 5% of a mixture of polyglycosides of formula (II):

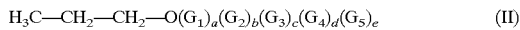

(II)

from 0% to 20% of a mixture of polyglycosides of formula (III):

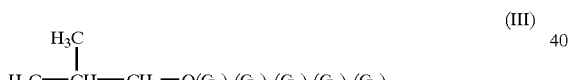

(III)

from 45% to 80% of a mixture of polyglycosides of formula (IV);

(IV)

from 10% to 40% of a mixture of polyglycosides of formula (V):

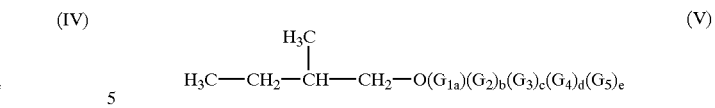

(V)

in which $G_1$, $G_2$, $G_3$, $G_4$, and $G_5$ are, independently of each other, residues of a saccharide selected from the group consisting of hexoses and pentoses; a, b, c, d, and e being equal to 0 or 1, the sum of a, b, c, d, and e being at least equal to 1 and wherein the combination of compounds I, II, III IV, and V, excluding any alkyl glycosides other than the compounds I, II, III, IV and V, represents 100%.

10. The adjuvant according to claim 8, comprising at least, on a weight basis:
   from 60% to 75% of a mixture of polyglycosides of formula (IV),
   from 25% to 40% of a mixture of polyglycosides of formula (V).

11. A composition, comprising at least, on a weight basis:
   10% to 60% of adjuvant according to claim 8
   40% to 90% of nonionic, anionic, amphoteric or cationic surfactants, or mixtures thereof.

12. The composition according to claim 11 comprising, on a weight basis:
   40% to 90% of nonionic surfactants.

13. A composition comprising, on a weight basis:
   10% to 60% of adjuvant according to claim 8
   40% to 90% of alkyl polyglycosides containing from 8 to 22 carbon atoms on the alkyl chain.

14. A composition, which comprises, on a weight basis:
   0.5% to 5% of adjuvant according to claim 8,
   2% to 7% of alkyl polyglycosides containing from 8 to 14 carbon atoms on the alkyl chain,
   1% to 10% of linear or branched alkanols containing from 2 to 5 carbon atoms, or mixtures thereof,
   0.1% to 3% of lipophilic active substances to be dissolved.

15. A composition comprising, on a weight basis:
   0.5% to 5% of adjuvant according to claim 8,
   1% to 10% of alkyl polyglycosides containing from 8 to 14 carbon atoms on the alkyl chain,
   1% to 10% of linear or branched alkanols containing from 2 to 5 carbon atoms, or mixtures thereof,
   0.1% to 2% of essential oil,
   0% to 0.5% of preserving agent.

16. The composition according to claim 15, wherein the essential oil is selected from the group consisting of pine oil, lemon oil, orange oil, mandarin oil, grapefruit oil, lavendar oil, mint oil, thyme oil, rosemary oil and eucalyptus oil.

17. The adjuvant according to claim 8 wherein the saccharide is selected from the group consisting of arabinose and xylose.

* * * * *

UNITED STATES PATENT AND TRADEMARK OFFICE
CERTIFICATE OF CORRECTION

PATENT NO. : 6,774,113 B2
DATED : August 10, 2004
INVENTOR(S) : Bertho et al.

It is certified that error appears in the above-identified patent and that said Letters Patent is hereby corrected as shown below:

Column 20,
Line 32, "by dilation." should be changed to -- by distillation. --

Signed and Sealed this

Nineteenth Day of July, 2005

JON W. DUDAS
*Director of the United States Patent and Trademark Office*